United States Patent
Hamburger et al.

[11] Patent Number: 6,087,947
[45] Date of Patent: *Jul. 11, 2000

[54] ALLERGEN DETECTOR SYSTEM AND METHOD

[75] Inventors: Robert N. Hamburger, 9485 La Jolla Shores Dr., La Jolla, Calif. 92037; Ruibo Wang; Jien-Ping Jiang, both of Tucson, Ariz.

[73] Assignee: Robert N. Hamburger, La Jolla, Calif.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/771,641

[22] Filed: Dec. 20, 1996

Related U.S. Application Data

[63] Continuation-in-part of application No. 08/679,706, Jul. 11, 1996, Pat. No. 5,646,597.

[51] Int. Cl.[7] .................................................. G08B 21/00
[52] U.S. Cl. ........................ 340/627; 340/670; 116/214; 250/564; 250/574; 356/438
[58] Field of Search ..................................... 340/627, 630, 340/628; 250/564, 565, 573, 574; 356/337, 339, 439, 438; 73/28.01, 28.04, 863.21–863.24; 116/214

[56] References Cited

U.S. PATENT DOCUMENTS

| | | | |
|---|---|---|---|
| 3,845,480 | 10/1974 | Steinbert | 340/236 |
| 3,867,640 | 2/1975 | Paulsen | 250/574 |
| 4,175,865 | 11/1979 | Horvath et al. | 340/630 |
| 4,226,533 | 10/1980 | Snowman | 340/630 |
| 4,583,859 | 4/1986 | Hall, II | 356/438 |
| 4,830,494 | 5/1989 | Ishikawa . | |
| 4,839,463 | 6/1989 | Fruengel | 250/574 |
| 5,001,463 | 3/1991 | Hamburger | 340/627 |
| 5,305,072 | 4/1994 | Sawada et al. | 356/336 |
| 5,315,115 | 5/1994 | Gerber . | |
| 5,383,024 | 1/1995 | Maxey et al. | 356/336 |
| 5,416,580 | 5/1995 | Trainer | 356/336 |
| 5,426,501 | 6/1995 | Hokanson et al. | 356/335 |
| 5,428,964 | 7/1995 | Lobdell . | |
| 5,646,597 | 7/1997 | Hambueger et al. | 340/627 |

FOREIGN PATENT DOCUMENTS

| | | |
|---|---|---|
| 03108635 | 5/1991 | Japan . |
| 8233728 | 9/1996 | Japan . |
| 1298658 | 4/1971 | United Kingdom . |
| 2044445 | 10/1980 | United Kingdom . |

OTHER PUBLICATIONS

"Simslin II—A Portable Airborne Dust Measuring Instrument Employing a Light Scattering Technique", C. Casswell et al., Conference: Proccedings of the Fourth WVU Conference on Coal Mine Electrotechnology, Aug. 2–4 1978.
Casswell et al., *Simslin II–A Portable Airbourne Dust Measuring Instrument Employing a Light Scattering Technique*, Aug. 1978, pp. 20-1-20-12.

*Primary Examiner*—Daniel J. Wu
*Attorney, Agent, or Firm*—Brown, Martin, Haller & McClain, LLP

[57] ABSTRACT

An allergen particle detecting apparatus has a sample area through which environmental air is directed. A light beam is directed through the air sample so that portions of the beam will be scattered if any particles are present in the path of the beam. A beam blocking device on the opposite side of the air sample is arranged to block all light except light scattered in a predetermined angular range corresponding to a predetermined allergen particle size range. Light transmitted through the blocking device is detected by a light detector and an alarm output signal is produced if the detected amount of light is above a predetermined level.

31 Claims, 3 Drawing Sheets

ALLERGEN DETECTOR SYSTEM AND METHOD

CROSS-REFERENCES TO RELATED APPLICATIONS

This application is a continuation-in-part of application Ser. No. 08/679,706 filed Jul. 11, 1996, now U.S. Pat. No. 5,646,597.

BACKGROUND OF THE INVENTION

The present invention is directed to a system and method for detecting airborne allergen particles and for providing an alarm or operating a filtering system if the detected amount of allergen particles is above a predetermined level.

Many individuals suffer from allergies to airborne particles such as dust, pollen and the like which are often present in the environmental air breathed by the individual. The majority of particulates to which many individuals are sensitive are typically in the 5 to 50 micron range. The presence of such particles in air breathed by sensitive or allergic individuals may give rise to symptoms such as asthma, coughing, sneezing, as well as skin rashes and anaphylaxis. Knowledge or warning of the presence of high levels of allergenic particles in the environmental air is helpful to such individuals, potentially enabling them to take medication, leave the area, or activate allergen removing filters, before the onset of serious symptoms.

In U.S. Pat. No. 5,001,463 of Hamburger an allergen particulate detecting apparatus is described in which air is blown through a passageway in which an allergen particle sensor is mounted for trapping allergen-sized particles. The output signal of the sensor is dependent on the amount of trapped particles, and an alarm is activated if the signal is above a predetermined level.

SUMMARY OF THE INVENTION

It is an object of the present invention to provide a new and improved allergen detection system and method.

According to one aspect of the present invention, an allergen particle detection system is provided which comprises a light source for directing a light beam through a sample of environmental air, a beam blocking assembly positioned in the light path on the opposite side of the air sample for blocking transmission of all light except the portion of light scattered in a predetermined angular range corresponding to a predetermined allergen particle size range of 0.5 micron to 500 microns, a detector positioned to receive light transmitted through the beam blocking assembly, and a control circuit connected to the detector for generating an alarm output signal if the detector output is above a predetermined level.

The alarm output signal may be used to activate an audible or visual alarm device, or to turn on a filtration and ventilation system including HEPA or allergen particle filters. The filtration system may be turned off as soon as the detected allergen particles have returned to a safe level. The apparatus may be relatively small, and may be conveniently designed for wall mounting.

The beam blocking assembly may comprise a circle of light blocking material centered on the optical axis and of predetermined diameter to block all unscattered light and light scattered at angles below a predetermined minimum angle which is scattered by particles larger than the largest allergen particle size, and an annular ring of light blocking material having an inner diameter corresponding to the predetermined maximum scattering angle, such that light scattered at angles larger than the maximum scattering angle is blocked. In a preferred embodiment, the dimensions of the blocking assembly were arranged to block all light except that scattered by particles in the size range of 5 microns to 50 microns, although a size range of up to 0.5 to 500 microns may alternatively be used.

In another embodiment of the invention, a two-part beam blocking assembly may be provided, comprising a first beam blocking device having a circle of light blocking material of predetermined diameter for blocking at least the unscattered portion of the light transmitted through the air sample, and a second beam blocking device having at least one pinhole for transmitting light in the predetermined angular range. Preferably, the blocking circle in the first device is dimensioned to block unscattered light and light scattered at angles below the minimum angle in the predetermined range. The second device preferably has one aperture centered on the optical axis with a diameter such that light scattered at angles above the maximum angle in the range is blocked.

According to another aspect of the present invention, a method of detecting allergen particles in the air is provided which comprises the steps of directing a light beam through a sample of environmental air so that light will be scattered by any particles in the air, blocking unscattered light and light scattered outside a predetermined angle range on the opposite side of the air sample, and transmitting only light within the predetermined range of scattering angle, detecting the transmitted light and producing a first output signal at a level proportional to the amount of light transmitted, and generating an alarm output signal if the first output signal is above a predetermined level.

This system and method readily discriminates between allergen size particles in the 5 to 50 micron range and larger, non-allergenic particles so as to produce an accurate indication of the allergen particle levels in a room or enclosed area. Preferably, the level at which the alarm signal is produced is adjustable. The apparatus can be readily connected to turn on auxiliary air cleaning appliances or filters such as HEPA filters.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENTS

Figure 1:
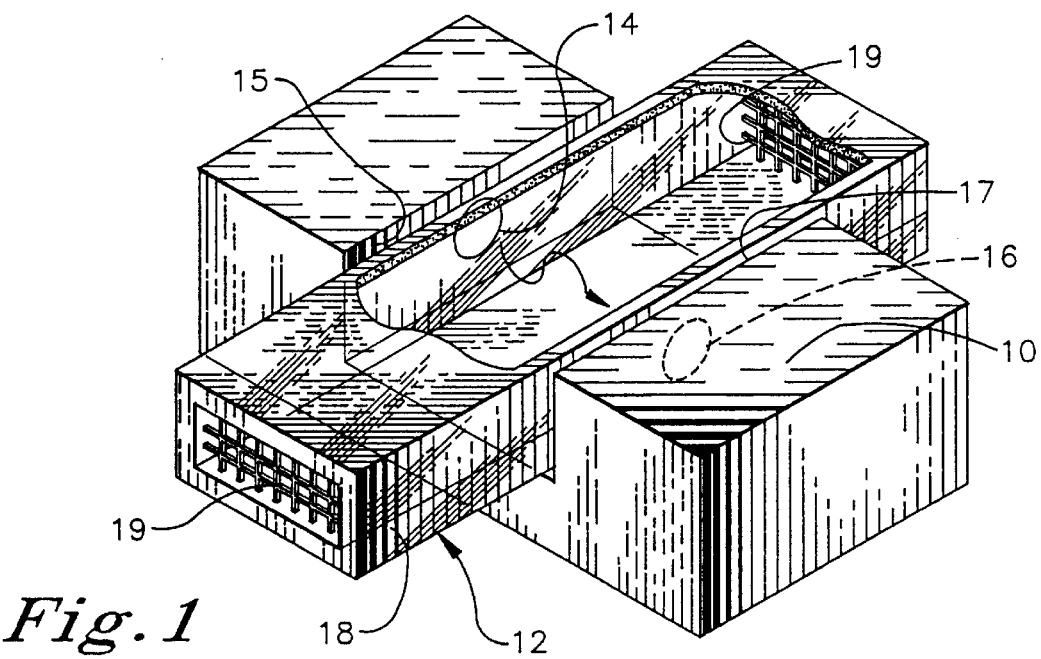
FIG. 1 is a perspective view of an allergen particle detector apparatus according to a first embodiment of the present invention.
Figure 2:
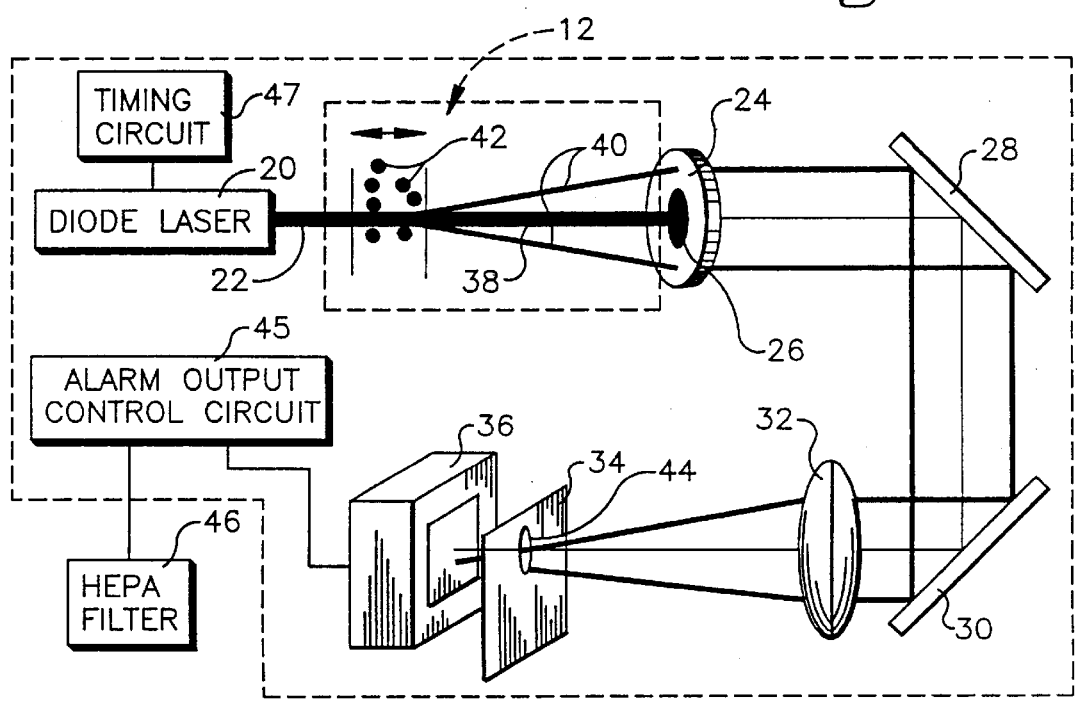
FIG. 2 is a schematic block diagram of the optical system.
Figure 3:
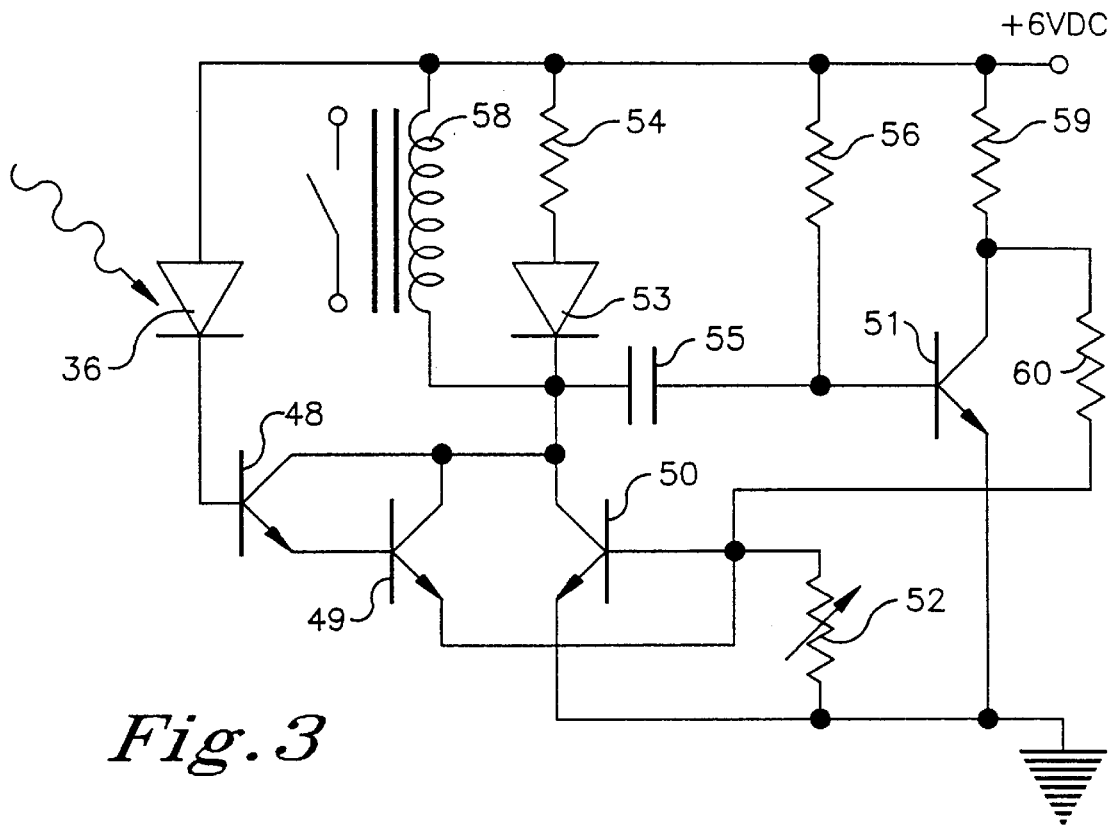
FIG. 3 is a circuit diagram of the electrical control circuit.
Figure 4:
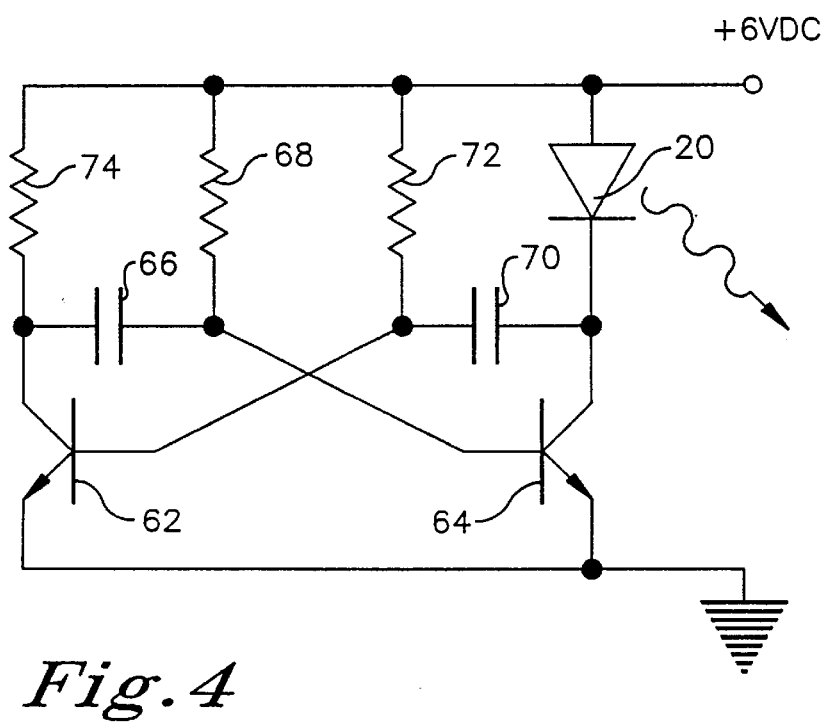
FIG. 4 is a diagram of the timing circuitry.
Figure 5:
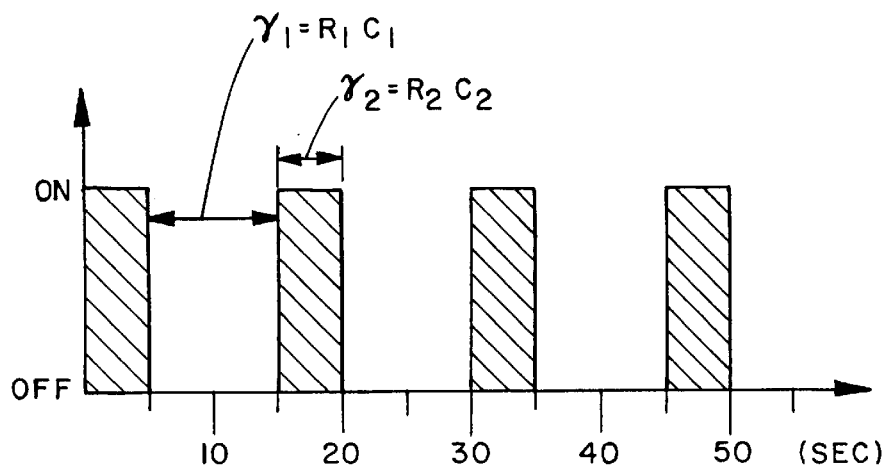
FIG. 5 is a timing diagram.

FIGS. 1 and 2 of the drawings illustrate an allergen particle detector apparatus according to a first embodiment of the present invention, while FIGS. 3–5 illustrate details of the electrical control circuitry. The apparatus basically comprises an outer housing 10 shaped to provide a passageway 12 across which a laser beam is directed from laser diode 20 through opening 14 in one side wall 15 of the passageway into opening 16 on the opposite side wall 17 of the passageway. A rectangular, transparent plastic tube or cell 18 is releasably mounted in the passageway. Tube 18 is open at opposite ends, and a grating or grille 19 is preferably mounted in each open end to prevent access to the interior of the tube. Tube 18 permits air flow through the passageway and through the path of the laser beam 22 directed across the passageway.

As best illustrated in FIG. 2, a beam blocking device 24 is mounted in the opening 16 facing the laser beam. The device 24 comprises a transparent circular flat glass plate with an opaque portion 26 at the center of the plate. Portion 26 may be produced by black paint, or a black plastic or metal insert at the center of the plate. The actual dimensions of the opaque blocking portion will be dependent on the cross-sectional shape and dimensions of the output beam of laser diode 20, and the particle size range to be detected by the apparatus. The laser diode may emit infrared light (0.8–1.0 micron) or visible light. In one embodiment of the invention a laser diode emitting at the wavelength of 670 nm. was used. This device has an output beam of elliptical shape, with a long axis of 3 mm and a short axis of 2 mm. The blocking portion 26 in this example will therefore also be of elliptical shape and larger dimensions than the laser diode output beam, to ensure all direct light is blocked, as well as light scattered at angles below a predetermined minimum angle, depending on the allergen particle size range to be detected.

The majority of allergen particles to which individuals may be sensitive are in the size range of 5 to 50 microns, although a small quantity of allergen particles may be found at sizes from 0.5 to 5 microns and from 50 to 500 microns. Thus, substantially all allergen particles will be found in the size range of 0.5 to 500 microns, with the maximum number being in the range of 5 to 50 microns. Therefore, the apparatus is preferably designed to detect particles in the size range of 0.5 to 500 microns, although it may alternatively be designed to detect particles in the range of 5 to 50 microns, since the majority of allergens will be in this size range.

The angle at which light is scattered by a particle will be dependent on the wavelength of the light and the size of the particle. Airborne particles of different sizes have quite different light scattering properties. Larger particles will scatter light at smaller angles. For a red to infrared light source in the wavelength range of 0.6 micron to 1.0 micron, the smallest scattering angle for a particle size range of 0.5 to 50 microns is about 40 to 50 (see *Electromagnetic Scattering*, R. L. Rowell and R. S. Stein, ed., p. 140, Gordon and Breach 1965). If the blocking device is at a distance of L from the air sample, the radius of the central blocking portion should be L * tan(5°), in order to block light scattered at angles less than 5°, i.e. light scattered by particles larger than 50 microns. The blocking device can therefore be arranged to block all light scattered by particles of size greater than 50 microns.

An extended light path or passageway is defined in the housing from blocking device 24. A first mirror 28 is positioned in the light path from device 24 for redirecting light in a first direction, and a second mirror 30 is positioned to intercept light reflected from mirror 28 and direct it back in the opposite direction via a lens 32 and a pinhole device 34 to a photodetector 36. The output of photodetector 36 is connected to electronics and timing circuitry which is described in more detail below in connection with FIGS. 3–5.

A portion 38 of the laser light beam directed across the passageway will pass straight to the blocking device 24 without scattering, while other portions 40 of the beam will encounter particles 42 and will be scattered at angles dependent on the particle size. The opaque central portion 26 of the blocking device is designed to block transmission of at least the unscattered portion 38 of the light beam, while all scattered portions at angles greater than 50 will be transmitted through the transparent peripheral portion of the device. Scattered portions of the beam will be reflected by mirrors 28,30 towards pinhole device 34. The pinhole device 34 comprises an opaque plate with a pinhole or opening 44 of predetermined diameter such that only light scattered in a predetermined angular range will pass through the pinhole. Opening 44 is centered on the optical axis 41.

The output of photodetector 36 is connected to an alarm output control circuit 45 which is illustrated in more detail in FIG. 3. The circuit 45 preferably has a suitable output for connection to an allergen filter device such as a HEPA filter 46, or an alarm device or the like. An audible alarm device or an alarm light emitting diode (LED) may be mounted within the housing. A timing circuit 47, illustrated in more detail in FIGS. 5 and 6, controls operation of the laser diode 20.

Airborne particles are typically present in the air in a large range of sizes. As noted above, allergen particles such as pollen, dust, mold spores and the like are predominantly in the size range from 5 to 50 microns. Larger particles typically cannot pass through the nose and do not normally cause any problem. The optical system as illustrated in FIG. 2 is designed to discriminate between light scattered by particles in the allergen size range and light scattered by larger particles outside that range. Only particles with sizes comparable to the wavelength of the incident light will have well pronounced scattering maxima in the forward direction of light propagation. For particles of sizes smaller than 0.5 micron, and a light source of wavelength 0.6 micron to 1.0 micron, the scattering angle will be larger than 27° (see Rowell and Stein, supra, and N. C. Wickramasinghe, *Light Scattering Functions for Small Particles with Applications in Astronomy*, page 233, Adam Hilger 1973). A pinhole or aperture 44 with a radius h such that light scattered at angles greater than 27° is blocked is placed on the optical axis. The opening 44 has a radius h, which can be calculated according to the following relationship:

$$h = \left[ (l_o - l_p) - \frac{l_o \cdot l_p}{f} \right] \tan\theta \qquad (1)$$

where θ is the scattering maximum angle (27° in this case), $l_o$ is the distance of the scattering particles from the lens, f is the focal length of the lens, and $l_p$ is the distance of the screen with the pinhole from the lens.

With this aperture diameter, only light scattered by particles in the allergen particle size range will be transmitted through the pinhole and detected by the photodetector. Alternatively, a pinhole with a very small aperture may be placed at an off-axis distance of h so as to intercept only light scattered at a predetermined angle, i.e. from particulates of a certain size. Plural pinholes may be positioned to intercept light scattered by different size particles within the range of interest. However, this arrangement is more complex and expensive, although it may be useful in systems where the ability to classify precise particle sizes is needed.

FIG. 3 illustrates the circuit for receiving the photodetector output and producing an alarm output signal if the output is above a predetermined level. FIGS. 4 and 5 illustrate timer circuitry for controlling the laser diode.

Referring first to FIG. 3, the output of photodiode or photodetector 36 is amplified by transistors 48,49. Transistors 50,51 act as level discriminators for determining when the output of the photodetector is above a preset level. The amplified output is connected to the base of transistor 50. Depending on the setting of a variable resistor 52, the input current can turn on transistor 50 and an alarm LED 53 which is mounted on the front panel of the housing. The switching on of transistor 50 also turns on relay 58, acting to switch on suitable filtering devices such as a HEPA filter as indicated in FIG. 2. The alarm LED is connected in series with resistor 54 to the 6 volt DC power supply. The sensitivity of the device can be set by adjusting the resistor 52. After transistor 50 is turned on, capacitor 55 starts to charge through charging resistor 56 and, after a time period set by the time constant ($\tau = R \times C$), the charge accumulated on the capacitor will turn on transistor 51. This will pull the current at the base of transistor 50 to zero and turn it off, thus shutting off the LED and the relay. Resistor 59 is connected in parallel with transistor 51, and resistor 59 is connected in series with the transistor 51. The value of capacitor 55 and resistor 56 will therefore determine the length of time that the LED and relay are on. The relay may be used to control a filtration and ventilation system or any device to filter out the allergen particles from the environmental air.

The timer circuit of FIG. 4 is used to control the laser diode 20 to turn on and off periodically, in order to lower the power consumption. Timing is provided by a bistable resistor circuit as illustrated in FIG. 4. When the power supply is turned on, current will flow to one of the two transistors 62,64, for example transistor 62. After transistor 62 is turned on, the capacitor 66 begins to be charged up through resistor 68. In this period there is no current flowing through the laser diode and the device is in the "OFF" mode. After a time period $\tau_1 = R_1 \times C_1$, the charges accumulated on capacitor 66 are sufficient to turn on the transistor 64, and this allows current to flow through the laser diode, switching the diode to the "ON" mode. At the same time, capacitor 70 will be charged up through resistor 72, and after a time period $\tau_2 = R_2 \times C_2$, the accumulated charges will turn on transistor 62 again, turning off the laser diode. This completes the cycle. The duty cycle of the timer circuit can be controlled by setting the values of capacitors 66 and 70 and resistors 68 and 72, as indicated in FIG. 5.

The housing is appropriately mounted in a room or other enclosed area where the level of allergen particulates is to be monitored. It may be designed for wall mounting so that only the air sampling area in passageway 12 is exposed. Environmental air will flow through tube 18 into the sampling area between the laser diode and the beam blocking device. If the air is free from any particulates, there will be no scattered light and the entire laser beam will be blocked by the central blocking region of the blocking device 24. Thus, no alarm signal will be generated. When there are airborne particulates 42 present, some of the laser beam will be scattered by those particles, and the scattered light will deviate from the original light path and will not be blocked by the blocking device 24. The amount of scattered light will be proportional to the number of particles 42 present.

All particles present in the air, including allergen particles, will cause scattering of the light, and the scattered light will travel along the light path and be reflected by mirrors 28 and 30 towards the lens 32 and pinhole device 34, which together form a discriminator to discriminate between allergen size particles and particles of other sizes. As explained in detail above, the pinhole or opening 44 is dimensioned such that only light scattered in a specific scattering angle range will pass through the pinhole, with light scattered in other directions being blocked. Thus, only light scattered by allergen-size particles passes through the pinhole and is detected by photodetector 36. If the amount of light detected is above a threshold set by adjustable resistor 52, the alarm LED 53 will be turned on and the relay 58 is actuated to turn on an allergen filtering device such as a HEPA filter, or a room air conditioning unit including a filtering device. Additionally, an audible alarm may be actuated. Preferably, an adjustment dial is provided on the housing to enable the user to adjust the resistance of resistor 52, and thus vary the sensitivity of the device. The device turns off when the detected allergen levels fall below the selected threshold value. A digital counter may be included to record the number of occurrences of allergen detection in a given period of time.

The two mirrors allow the light path within the housing to be extended, improving sensitivity. A system of more sensitivity may be provided by directing the light beam around the periphery of a room with appropriately positioned mirrors.

If desired, a timer circuit may be added to the system. This will provide a suitable alarm signal if the air is not cleaned within a certain time period after the filter unit is turned on, indicating a potential failure of the room filtering system. The control circuit of FIG. 3 may be a hard-wired device as illustrated or may alternatively be made as a printed circuit board in a simplified structure. This will take up less space within the housing and will reduce the problem of cross-talk between the electrical components. The entire device may be run from a single rechargeable 9-volt battery or other batteries, or may be connectable to a main power supply.

This apparatus enables up to 99% of airborne allergen particles to be detected, while larger, non-allergenic particles are not detected. For the safety of users, the clear plastic tube 18 is mounted in the air passageway 12 in the housing. The tube 18 is designed to be readily removable at periodic intervals when build up of dust on the internal surfaces of the tube causes a problem. At this point, it can be slid out of the passageway for cleaning or replacement with a new tube. The tube will prevent insertion of fingers or mirrors into the laser beam, making the device essentially child-proof. The rectangular design of the tube avoids unwanted distortion of the laser beam passing through the transparent side walls of the tube.

The laser pulse period may be set by the user as desired, to periods of 1 second, 1 minute, 10 minutes, 20 minutes, and so on, using an appropriate setting dial provided on an outer face of the housing. If the laser pulse length is set to be 10 seconds, then the setting dial will have sampling settings of continuous (the 1 second off setting is equivalent to continuous operation), 10 minutes per hour, 1 minute per hour, 30 seconds per hour, and so on.

Instead of an on-axis pinhole of predetermined diameter for transmitting all light within the desired range, as described above, the discriminator or pinhole device 34 may alternatively be provided with a plurality of very small pinholes at predetermined off-axis positions for transmitting only light at a predetermined scattering angle. Thus, each pinhole would correspond to a predetermined angle in the desired range.

Figure 6:
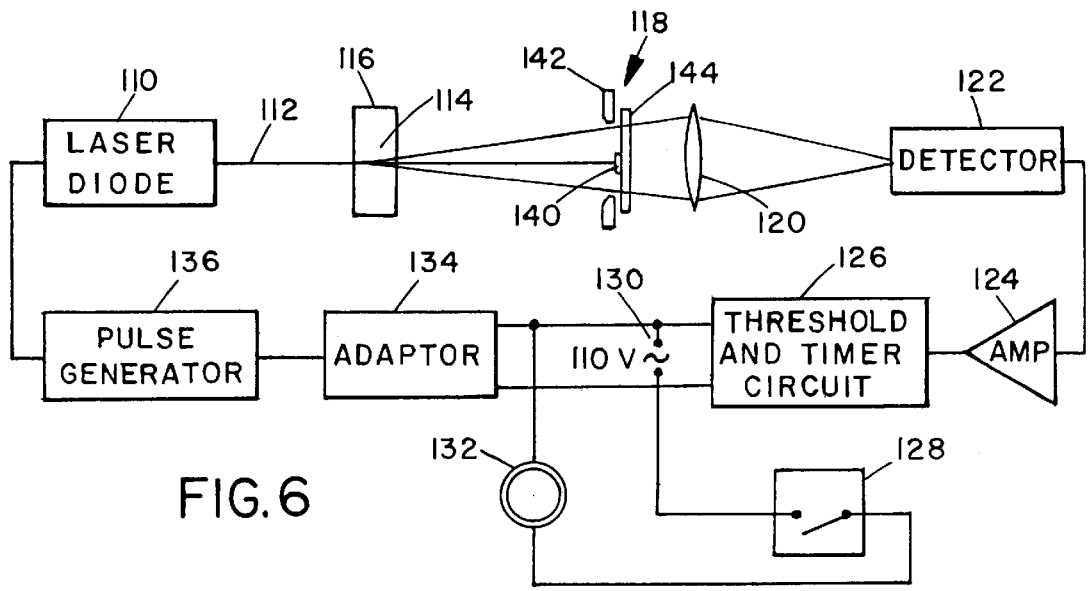
FIG. 6 is a block diagram of an allergen detector system according to a second embodiment of the invention.
Figure 7:
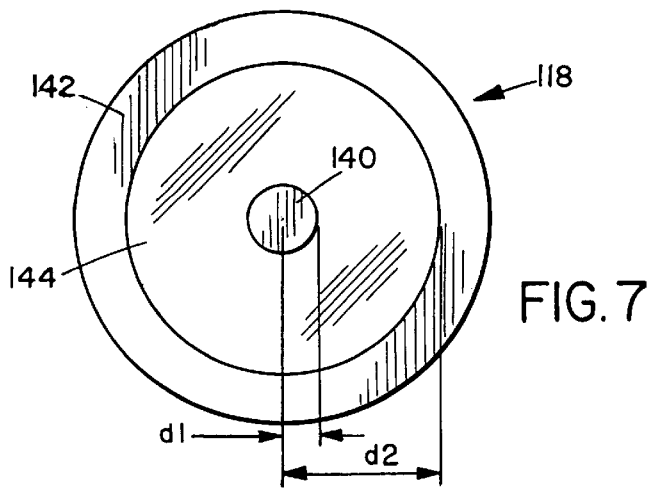
FIG. 7 is a front elevational view of the discriminator device of FIG. 6.

FIGS. 6 and 7 of the drawings illustrate an allergen detecting apparatus according to a second embodiment of the invention. In this apparatus, a laser diode or other light source 110 directs a light beam 112 across an environmental air sample 114 in a protective cell 116, which may be an open ended plastic tube or the like as in the previous embodiment. It is not essential that the air sample be enclosed within a protective cell or the like, but this is preferred for safety reasons. A beam blocking device or discriminator 118 is positioned in the light path after the air sample for blocking transmission of the direct light beam as well as light scattered outside a predetermined angular range corresponding to the allergen particle size range to be detected, as discussed above in connection with the first embodiment, and as also discussed in more detail below.

Lens 120 is positioned behind blocking device 118 in order to focus light transmitted by the device 118 onto a detector 122. The output of detector 122 is connected via amplifier 124 to a threshold and timer circuit 126. If the output of detector 122 is above a predetermined threshold, relay switch 128 is closed to connect power supply 130 to the air filter 132, which may be any suitable HEPA filter as in the previous embodiment. The power supply is also connected via adapter 134 and pulse generator 136 to the laser diode, so that the laser emits a pulsed beam of light rather than being on continuously. The laser will be timed to emit pulses of light at predetermined intervals in the same way as described above in connection with the first embodiment.

Although a laser diode in the infrared or visible light range is used as the light source in the preferred embodiment of the invention, other light sources may be used such as other types of laser emitters, for example a He—Ne laser with a wavelength of 0.6328 micron, or other light sources with collimators for producing a collimated light beam, such as light emitting diodes in the visible or infrared light range. The light is preferably infrared, but may alternatively be visible light.

In this embodiment, the discriminator or blocking device is simplified and is provided at one position rather than two spaced positions in the optical system as in the previous embodiment. Additionally, the mirrors which are used to fold the light path in the first embodiment so as to produce a smaller device, are eliminated in this embodiment in which the light path is straight through the device. The discriminator 118 comprises a plain glass disc 138 having a central circular portion 140 which is painted black to block light. An annular ring 142 of light blocking material is placed in front of disc 138. Alternatively, the disc itself may be painted black around a corresponding annular area. This defines an annulus 144 through which light will be transmitted. The annulus 144 will have a predetermined inner diameter d1 corresponding to the diameter of the black circle 140, and a predetermined outer diameter d2 corresponding to the inner diameter of ring 142, as best illustrated in FIG. 7. The dimensions d1 and d2 will be determined based on the particle size range to be detected. The majority of allergen particles are in the size range of 0.5 to 50 microns. These will scatter light in the range of around 5o to 27o, as described above in connection with the first embodiment. The diameter d1 is therefore determined from the relationship L * tan(5°). The diameter d2 is determined from L * tan(27°), where L is the distance of the discriminator 118 from the sensitive region or air sample. With these dimensions, the device 118 will transmit only light scattered in the range of 5o to 27o by particles in the range from 0.5 to 50 microns. The dimensions can be varied dependent on the desired particle size range to be detected, which may be expanded to 0.5 to 500 microns if desired, although the majority of allergen particles are found in the range from 0.5 to 50 microns.

The allergen particle detector of this invention has the advantage that only allergen-size particles are detected, due to the design of the optical system for eliminating light scattered by particles of sizes outside the allergen size range of 0.5 to 50 microns. The allergen detection level may be readily adjusted by the user. The apparatus is easy and inexpensive to manufacture, and simple to operate. It provides real time, accurate detection of excessive levels of allergen particles in the air, providing a warning to sensitive individuals who may need medication and also allowing allergen filtering equipment to be activated under such conditions to clean the air.

Although preferred embodiments of the present invention have been described above by way of example only, it will be understood by those skilled in the field that modifications may be made to the disclosed embodiments without departing from the scope of the invention, which is defined by the appended claims.

We claim:

1. An allergen detecting apparatus for detecting the presence of allergen particles in environmental air, comprising:
    an outer housing having a passageway for airflow through the housing;
    a light source on one side of the passageway for directing a light beam through the air passing through the passageway, wherein said light source defines an optical axis;
    beam blocking means on the other side of the passageway in the path of the light beam for transmitting light travelling in a predetermined scattering angle range and blocking transmission of all light outside said scattering angle range, wherein said beam blocking means comprises a first light blocking device centered on said optical axis for blocking light transmitted at angles less than a predetermined minimum scattering angle, and a second light blocking device for blocking light scattered at angles greater than a predetermined maximum scattering angle;
    a detector positioned in the light path after the beam blocking means for detecting light transmitted through the beam blocking means and producing an output signal proportional to the amount of light transmitted; and
    a control circuit connected to the detector output for generating an alarm output signal if the detector output is above a predetermined level.

2. A method of detecting allergen particles in the air, comprising the steps of:
    directing a light beam of substantially singular wavelength through a sample of environmental air, whereby portions of the light beam will be scattered by any particles present in the air sample;
    detecting light scattered in a predetermined angular range corresponding to a predetermined allergen particle size range; and
    producing an output signal proportional to the amount of light scattered in said predetermined angular range.

3. A method of detecting allergen particles in the air, comprising the steps of:
    providing a sample of environmental air;
    detecting any particles in the air in a predetermined allergen particle size range;
    producing an output signal if the detected number of particles is above a predetermined level; and
    switching on an air filtering device for removing allergen particles from the air in response to said output signal.

4. A method of detecting the quantity of allergen particles in the air, comprising the steps of:

directing environmental air to flow through a sample area;

directing a light beam of substantially singular wavelength transversely through the air flowing through the sample area, whereby a portion of the light beam will be scattered by any particles present in the path of the light beam;

blocking a first portion of the light beam on the opposite side of the passageway and transmitting a second predetermined portion of the light beam along a light path with a discriminating device;

the second predetermined portion of the light beam comprising all light scattered within a predetermined angular range by allergen-size particles in said sample area;

detecting the amount of light transmitted through the discriminating device; and producing an output alarm signal if the amount of light detected is above a predetermined level.

5. The method as claimed in claim 4, wherein the step of blocking scattered portions of the light beam outside the predetermined angular range comprises placing a light blocking device in the light path with an annular aperture of predetermined dimensions for transmitting light traveling in the predetermined angular range.

6. The method as claimed in claim 4, wherein the predetermined angular range is 4° to 27°.

7. The method as claimed in claim 4, including the step of using the output alarm signal to activate an allergen filtering device.

8. The method as claimed in claim 7, including the step of switching off the allergen filtering device when the light detected falls below the predetermined level.

9. An allergen detecting apparatus for detecting the presence of allergen particles in environmental air, comprising:

a light source for directing a light beam of substantially singular wavelength in a light path through a sample of environmental air, whereby portions of the light beam will be scattered by any particles present in the air;

a beam blocking device in the light path for transmitting only light scattered in a predetermined angular range corresponding to a predetermined allergen particle size range; and a detector positioned to detect light transmitted by said beam blocking device and producing an output proportional to the amount of light received.

10. The apparatus as claimed in claim 9, including a lens for focusing light transmitted by the beam blocking device onto the detector.

11. The apparatus as claimed in claim 9, including a control circuit connected to the output of the detector for generating an alarm output signal if the detector output is above a predetermined level.

12. The apparatus as claimed in claim 11, including an air filter for filtering allergen size particles from environmental air, the air filter having a switch connected to the control circuit for switching on the air filter in response to said alarm output signal.

13. The apparatus as claimed in claim 9, wherein the beam blocking device is adapted to transmit light scattered by allergen particles in the size range of 0.5 to 500 microns.

14. The apparatus as claimed in claim 13, wherein the beam blocking device is adapted to transmit light scattered by allergen particles in the size range of 0.5 to 50 microns.

15. The apparatus as claimed in claim 9, wherein said light source has a central optical axis and the blocking device comprises a circular beam blocking member of predetermined diameter centered on said optical axis, said beam blocking member being opaque to light of the wavelength transmitted by said light source, and said predetermined diameter being at least equal to the diameter of the light beam transmitted by said light source, whereby at least portions of the light beam which are not scattered during passage through the air sample are blocked by said beam blocking member.

16. The apparatus as claimed in claim 15, wherein said predetermined diameter is greater than the diameter of said unscattered light beam, and said diameter is sufficient to block light scattered at angles below a predetermined minimum angle.

17. The apparatus as claimed in claim 15, wherein the minimum angle is 4°.

18. The apparatus as claimed in claim 15, wherein the light blocking device further comprises an annular ring of light blocking material centered on said optical axis and surrounding said circular beam blocking member, the annular ring having a predetermined inner diameter greater than the diameter of said circular member for blocking light scattered at angles greater than a predetermined maximum scattering angle.

19. The apparatus as claimed in claim 18, wherein the maximum scattering angle is 27°.

20. An allergen detecting apparatus for detecting the presence of allergen particles in environmental air, comprising:

an outer housing having a passageway for air flow through the housing;

a light source on one side of the passageway for directing a light beam of substantially singular wavelength through the air passing through the passageway;

beam blocking means on the other side of the passageway in the path of the light beam for transmitting light traveling in a predetermined scattering angle range and blocking transmission of all light outside said scattering angle range;

a detector positioned in the light path after the beam blocking means for detecting light transmitted through the beam blocking means and producing an output signal proportional to the amount of light transmitted; and a control circuit connected to the detector output for generating an alarm output signal if the detector output is above a predetermined level.

21. The apparatus as claimed in claim 20, including a HEPA filter connected to said control circuit and having a switch for switching on the HEPA filter in response to said alarm output signal.

22. The apparatus as claimed in claim 20, including first and second mirrors in the light path between the blocking means and the detector for reflecting light traveling on the light path through 180°.

23. The apparatus as claimed in claim 20, including an alarm indicating device connected to said control circuit and responsive to said alarm output signal and having an alarm condition indicator which is actuated by said alarm output signal.

24. The apparatus as claimed in claim 23, wherein said alarm indicating device is a light emitting diode.

25. The apparatus as claimed in claim 20, including a transparent plastic tube removably mounted in the passageway, the tube having opposite, open ends for air flow through the tube.

26. The apparatus as claimed in claim 25, including a grating mounted over each open end of the tube.

27. The apparatus as claimed in claim 20, wherein the light source is a laser diode.

28. The apparatus as claimed in claim 27, including a timing circuit connected to the laser diode to control the diode to pulse on and off at predetermined time intervals.

29. The apparatus as claimed in claim 20, including an adjustment device for adjusting said predetermined level.

30. The apparatus as claimed in claim 29, wherein the adjustment device comprises a variable resistor.

31. The apparatus as claimed in claim 29, wherein the adjustment device includes a digital counter to record the number of occurrences of allergen detection in a given duration of time.

* * * * *